(12) United States Patent
Bruce et al.

(10) Patent No.: US 7,521,253 B2
(45) Date of Patent: Apr. 21, 2009

(54) METHOD FOR MULTIPLE TARGET ASSAY FOR DRUG DISCOVERY

(75) Inventors: Richard H. Bruce, Los Altos, CA (US); Steven Rosenberg, Oakland, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 501 days.

(21) Appl. No.: 10/303,500

(22) Filed: Nov. 22, 2002

(65) Prior Publication Data

US 2003/0186455 A1    Oct. 2, 2003

Related U.S. Application Data

(63) Continuation-in-part of application No. 10/114,611, filed on Apr. 1, 2002, now Pat. No. 7,141,210.

(51) Int. Cl.
*G01N 33/00* (2006.01)
(52) U.S. Cl. .................. 436/147; 436/164; 436/179; 436/180
(58) Field of Classification Search .............. 436/180, 436/179, 164, 147
See application file for complete search history.

(56) References Cited

U.S. PATENT DOCUMENTS

| | | | |
|---|---|---|---|
| 5,486,337 A | 1/1996 | Ohkawa | |
| 5,967,659 A | 10/1999 | Plotnikov et al. | 374/11 |
| 6,079,873 A | 6/2000 | Cavicchi et al. | 374/10 |
| 6,096,559 A | 8/2000 | Thundat et al. | 436/147 |
| 6,193,413 B1 | 2/2001 | Lieberman | 374/45 |
| 6,331,074 B1 | 12/2001 | Kimura | |
| 6,380,605 B1 | 4/2002 | Verhaegen | |
| 6,436,346 B1 | 8/2002 | Doktycz et al. | |
| 6,545,334 B2 | 4/2003 | Verhaegen | |
| 6,648,503 B2 | 11/2003 | Tanaka et al. | |
| 6,843,586 B1 | 1/2005 | Verhaegen | |
| 7,141,210 B2 | 11/2006 | Bell et al. | |
| 7,147,763 B2 | 12/2006 | Elrod et al. | |
| 7,416,897 B2 | 8/2008 | Bruce et al. | |
| 7,419,835 B2 | 9/2008 | Torres et al. | |
| 7,473,030 B2 | 1/2009 | Bruce et al. | |

(Continued)

FOREIGN PATENT DOCUMENTS

DE    19947788 A1    4/2001

(Continued)

OTHER PUBLICATIONS

U.S. Appl. No. 10/114,611, filed Apr. 1, 2002, Alan G. Bell.

(Continued)

*Primary Examiner*—Sam P Siefke
(74) *Attorney, Agent, or Firm*—Leading-Edge Law Group, PLC; James T. Beran

(57) ABSTRACT

A method is provided for multiple target screening for drug assays utilizing a nanocalorimeter. The method includes depositing a drop containing a plurality of drug targets and another drop containing a plurality of drug candidates upon a test substrate. The drops are merged and a determination is made as to whether a reaction has occurred between the drops. If such a reaction has occurred, the reacting drug targets and drug candidates are tested individually.

20 Claims, 2 Drawing Sheets

U.S. PATENT DOCUMENTS

| | | | |
|---|---|---|---|
| 7,473,031 | B2 | 1/2009 | Wolkin et al. |
| 2002/0003830 | A1 | 1/2002 | Tanaka et al. |
| 2002/0021740 | A1 | 2/2002 | Danley |
| 2003/0044800 | A1* | 3/2003 | Connelly et al. ............ 435/6 |
| 2003/0152128 | A1 | 8/2003 | Verhaegen |
| 2004/0038227 | A1 | 2/2004 | Verwaerde et al. |
| 2004/0038228 | A1 | 2/2004 | Verhaegen |
| 2005/0112710 | A1 | 5/2005 | Torres et al. |
| 2005/0112766 | A1 | 5/2005 | Bruce et al. |
| 2005/0238080 | A1 | 10/2005 | Wolkin et al. |
| 2005/0254552 | A1 | 11/2005 | Bruce et al. |
| 2005/0254994 | A1 | 11/2005 | Bell et al. |
| 2005/0265898 | A1 | 12/2005 | Bell et al. |
| 2006/0078999 | A1 | 4/2006 | Bell et al. |

FOREIGN PATENT DOCUMENTS

| | | | |
|---|---|---|---|
| WO | WO9954730 | * | 10/1999 |
| WO | WO 01/85978 A2 | | 11/2001 |

OTHER PUBLICATIONS

Washizu, M., "Electrostatic Actuation of Liquid Droplets for Microreactor Applications", IEEE Transactions on Industry Applications, vol. 34, No. 4, Jul./Aug. 1998, pp. 732-737.

Pierce, M.M., Raman, C.S., Nall, B.T., "Isothermal Titration Calorimetry of Protein-Protein Interactions", Methods, vol. 19, 1999, pp. 213-221.

Pollack, M.G., Fair, R.B., and Shenderov, A.D., "Electrowetting-based actuation of liquid droplets for microfluidic applications", Applied Physics Letters, vol. 77, No. 11, Sep. 11, 2000, pp. 1725-1726.

Jones, T.B., Gunji, M., Washizu, M., Feldman, M.J., "Dielectrophoretic liquid actuation and nanodroplet formation", Journal of Applied Physics, vol. 89, No. 2, Jan. 15, 2001, pp. 1441-1448.

Fowler, J., Moon, H., and Kim, C.-J., "Enhancement of Mixing by Droplet-Based Microfludics", IEEE, 0-7803-7185-2/02, pp. 97-100.

Johannessen, E.A., Weaver, J.M.R., Cobbold, P.H., and Cooper, J.M., "Heat conduction nanocalorimeter of pl-scale single cell measurements", Applied Physics Letters, vol. 80, No. 11, Mar. 18, 2002, pp. 2029-2031.

Johannessen, E.A., Weaver, J.M.R., Cobbold, P.H., and Cooper, J.M., A Suspended Membrane Nanocalorimeter for Ultralow Volume Bioanalysis, IEEE Transactions on Nanobioscience, vol. 1, No. 1, Mar. 2002, pp. 29-36.

Office communication in U.S. Appl. No. 11/167,748, mailed May 11, 2007, 24 pages, published in PAIR.

Amendment with Information Disclosure in U.S. Appl. No. 11/167,748, dated Aug. 10, 2007, 16 pages, published in PAIR.

Office communication in U.S. Appl. No. 11/167,746, mailed Jul. 9, 2007, 12 pages, published in PAIR.

Amendment with Information Disclosure in U.S. Appl. No. 11/167,746, dated Apr. 17, 2007, 21 pages, published in PAIR.

Office communication in U.S. Appl. No. 11/167,746, mailed Sep. 14, 2007, 4 pages, published in PAIR.

Amendment After Final Rejection in U.S. Appl. No. 11/167,746, dated Sep. 7, 2007, 13 pages, published in PAIR.

Amendment with Request for Continued Examination in U.S. Appl. No. 11/167,746, dated Oct. 3, 2007, 12 pages, published in PAIR.

Office communication in U.S. Appl. No. 11/167,748, mailed Feb. 15, 2008, 13 pages, published in PAIR.

Office communication in U.S. Appl. No. 11/167,746, mailed Dec. 28, 2007, 8 pages, published in PAIR.

Amendment with Information Disclosure in U.S. Appl. No. 11/167,746, dated Mar. 21, 2008, 13 pages, published in PAIR.

Office communication in U.S. Appl. No. 11/167,748, mailed Jun. 20, 2008, 13 pages, published in PAIR.

Amendment After Final Rejection in U.S. Appl. No. 11/167,748, dated Aug. 20, 2008, 13 pages, published in PAIR.

Notice of Allowance and Fee(s) Due in U.S. Appl. No. 11/167,748, dated Sep. 29, 2008, 9 pages, published in PAIR.

Office communication in U.S. Appl. No. 11/167,746, mailed Jun. 27, 2008, 7 pages, published in PAIR.

Office communication in U.S. Appl. No. 11/167,746, mailed Aug. 11, 2008, 2 pages, published in PAIR.

Amendment in U.S. Appl. No. 11/167,746, dated Sep. 2, 2008, 18 pages, published in PAIR.

Office communication in U.S. Appl. No. 11/149,632, mailed Jun. 10, 2008, 11 pages, published in PAIR.

Amendment in U.S. Appl. No. 11/149,632, dated Sep. 5, 2008, 23 pages, published in PAIR.

Office communication in U.S. Appl. No. 11/149,632, mailed Dec. 8, 2008, 14 pages, published in PAIR.

Request for Reconsideration with Information Disclosure in U.S. Appl. No. 11/149,632, submitted Jan. 6, 2009, 7 pages, published in PAIR.

* cited by examiner

METHOD FOR MULTIPLE TARGET ASSAY FOR DRUG DISCOVERY

This application is a continuation in part of U.S. application Ser. No. 10/114,611, filed Apr. 1, 2002, the disclosure of which is totally incorporated by reference.

CROSS REFERENCE TO RELATED APPLICATIONS

The following copending application, U.S. application Ser. No. 10/303,446, filed Nov. 22, 2002, titled "Apparatus and Method for Lead Profiling Assay", now abandoned, is assigned to the same assignee of the present application. The entire disclosure of this application is totally incorporated herein by reference in its entirety.

INCORPORATION BY REFERENCE

The following U.S. patents are fully incorporated herein by reference: U.S. Pat. No. 5,967,659 ("Ultrasensitive Differential Microcalorimeter with User-selected Gain Setting" to Plotnikov et al.); U.S. Pat. No. 6,079,873 ("Micron-scale Differential Scanning Calorimeter on a Chip" to Cavicchi et al.); U.S. Pat. No. 6,096,559 "Micromechanical Calorimetric Sensor" to Thundat et al.); and U.S. Pat. No. 6,193,413 ("System and Method for an Improved Calorimeter for Determining Thermodynamic Properties of Chemical and Biological Reactions" to Lieberman).

BACKGROUND OF THE INVENTION

This invention relates generally to a method for performing target assays for drug discovery, and more specifically, to a method for simultaneous screening of multiple drug targets for increasing the efficiency of the screening process and to a method of screening drug candidates with non-target molecules to anticipate selectivity of reaction of the drug candidates to the target molecules over non-target molecules.

In recent years, researchers and companies have turned to combinatorial methods and techniques for synthesizing, discovering and developing new compounds, materials, and chemistries. For example, pharmaceutical researchers have turned to combinatorial libraries as sources of new lead compounds for drug discovery. As another example, Symyx Technologies® is applying combinatorial techniques to materials discovery in the life sciences, chemical, and electronics industries. Consequently, there is a need for tools that can measure reactions and interactions of large numbers of small samples in parallel, consistent with the needs of combinatorial discovery techniques. Preferably, users desire that these tools enable inexpensive measurements and minimize contamination and cross-contamination problems. In addition there has been an explosion in the number of potential drug targets due to the accelerated implementation of genomics technologies and the completion of the Human Genome sequence.

In some cases, the sample to be studied is precious, and it might not be acceptable to use the relatively large amount of material required by a standard microcalorimeter to perform only one measurement. For example, one may desire to study a natural extract or synthesized compound for biological interactions, but in some cases the available amount of material at concentrations large enough for calorimetry might be no more than a few milliliters. Performing a measurement in standard microcalorimeters, such as those sold, for example, by MicroCal® Inc. (model VP-ITC) or Calorimetry Sciences Corporation® (model CSC-4500), requires about 1 ml of sample, which means that one would possibly be faced with using a majority or all of the precious material for one or a small series of measurements. Tools that enable calorimetric measurements with much smaller sample sizes would be helpful in overcoming this limitation.

One of the most popular uses of combinatorial techniques to date has been in pharmaceutical research. Pharmaceutical researchers have turned to combinatorial libraries as sources of new lead compounds for drug discovery. A combinatorial library is a collection of chemical compounds which have been generated, by either chemical synthesis or biological synthesis, by combining a number of chemical "building blocks" as reagents. For example, a combinatorial polypeptide library is formed by combining a set of amino acids in every possible way for a given compound length (i.e., the number of amino acids in a polypeptide compound). Millions of chemical compounds can theoretically be synthesized through such combinatorial mixing of chemical building blocks.

Once a library has been constructed, it must be screened to identify compounds, which possess some kind of biological or pharmacological activity. For example, screening can be done with a specific biological compound, often referred to as a target that participates in a known biological pathway or is involved in some regulatory function. The library compounds that are found to react with the targets are candidates for affecting the biological activity of the target, and hence a candidate for a therapeutic agent.

A variety of measurement approaches has been used to screen combinatorial libraries for lead compounds, one of which is the competitive binding assay. In this assay, a marker ligand, often the natural ligand in a biological pathway, is identified that will bind well with the target protein. The assay often requires the chemical attachment of a fluorescent molecule to this marker ligand such that the fluorescent molecule does not affect the manner in which the marker ligand reacts with the target protein. Alternatively, the ligand could be radioactively labeled or labeled with a chemiluminescent molecule. To operate an inhibitor assay, the target protein is exposed to a mixture of the test ligands and marker ligand often in microtitre wells. After a time for reaction, the wells are rinsed such that free marker ligand is washed away. In wells where the target protein and the test ligand have reacted, the test ligand has blocked the active site of the target protein so the marker ligand cannot react and is washed away, while in wells where the target protein and test ligand have not reacted, the marker ligand has bound to the target protein and is not washed away. By investigating the wells for the presence of fluorescence after the washing, reactions of test ligands and target proteins can be determined as having occurred in wells where reduced fluorescence is observable relative to control wells to which no test ligands have been added.

However, the competition binding assay requires time and expense to develop the labeled reagents and assay. The principal components that need development are discovering a marker ligand and attaching a fluorophore to the marker in a manner that does not affect its reaction with the target protein. Attaching the fluorescent marker can often take 3 months of development or more and cost $250 k or more once the marker ligand is identified. An assay method that avoids such assay development, such as measuring the heat of the reaction with calorimetry, would eliminate this cost and time delay in the discovery process.

The following disclosures may be relevant and/or helpful in providing an understanding of some aspect of the present invention:

In Plotnikov et al., U.S. Pat. No. 5,967,659 ("Ultrasensitive Differential Microcalorimeter with User-selected Gain Setting"), a differential calorimeter is disclosed that includes sample and reference cells, a thermal shield surrounding the cells, heating devices thermally coupled to the thermal shield and the cells, a temperature monitoring system, and a control system. The temperature monitoring system monitors the temperature of the shield, cell temperatures, and temperature differentials between the cells and the shield. The control system generates output signals for control of the heating devices, with a gain setting and scan rate selected by means of a user interface. Output control signals are functions of input temperature signals and the user-selected gain setting, as well as functions of input temperature signals and the user-selected scan rate using a mapping function stored in memory.

In Cavicchi et al., U.S. Pat. No. 6,079,873 ("Micron-scale Differential Scanning Calorimeter on a Chip"), a differential scanning microcalorimeter produced on a silicon chip enables microscopic scanning calorimetry measurements of small samples and thin films. The chip, fabricated using standard CMOS processes, includes a reference zone and a sample zone. The reference and sample zones may be at opposite ends of a suspended platform or may reside on separate platforms. Each zone is heated with an integrated polysilicon heater. A thermopile consisting of a succession of thermocouple junctions generates a voltage representing the temperature difference between the reference and sample zones.

In Thundat et al., U.S. Pat. No. 6,096,559 ("Micromechanical Calorimetric Sensor"), a calorimeter sensor apparatus utilizes microcantilevered spring elements for detecting thermal changes within a sample containing biomolecules which undergo chemical and biochemical reactions. The spring element includes a bimaterial layer of chemicals on a coated region on at least one surface of the microcantilever. The chemicals generate a differential thermal stress across the surface upon reaction of the chemicals with an analyte or biomolecules within the sample due to the heat of chemical reactions in the sample placed on the coated region. The thermal stress across the spring element surface creates mechanical bending of the microcantilever. The spring element has a low thermal mass to allow detection and measuring of heat transfers associated with chemical and biochemical reactions within a sample place on or near the coated region. Deflections of the cantilever are detected by a variety of detection techniques.

In Lieberman, U.S. Pat. No. 6,193,413 ("System and Method for an Improved Calorimeter for Determining Thermodynamic Properties of Chemical and Biological Reactions") a microcalorimeter includes a thin amorphous membrane anchored to a frame within an environmental chamber. Thermometers and heaters are placed on one side of a thermal conduction layer mounted on the central portion of the membrane. Samples are placed on two such membranes; each sample is heated and its individual heat capacity determined. The samples are then mixed by sandwiching the two microcalorimeters together to cause a binding reaction to occur. The amount of heat liberated during the reaction is measured to determine the enthalpy of binding.

SUMMARY OF THE INVENTION

Briefly stated, and in accordance with one aspect of the present invention, there is disclosed a method for multiple target screening for drug assays utilizing a nanocalorimeter. The method includes depositing a drop containing a plurality of drug targets and another drop containing a plurality of drug candidates upon a test substrate. The drops are merged and a determination is made as to whether a reaction has occurred between the drops. If such a reaction has occurred, the reacting drug targets and drug candidates are tested individually.

BRIEF DESCRIPTION OF THE DRAWINGS

The foregoing and other features of the instant invention will be apparent and easily understood from a further reading of the specification, claims and by reference to the accompanying drawings in which:

DETAILED DESCRIPTION OF THE INVENTION

Figure 1:
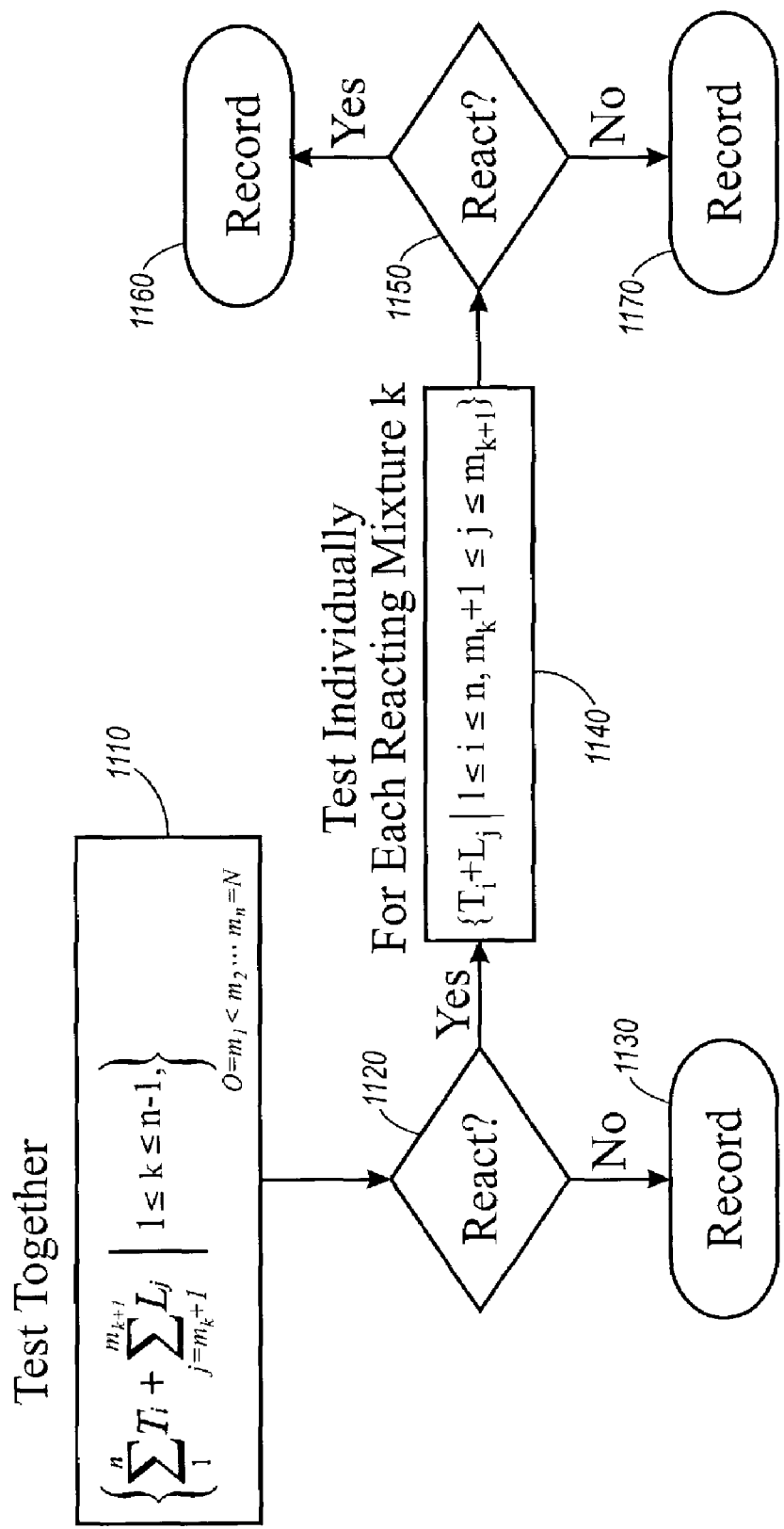
FIG. 1 is a flow chart illustrating an embodiment of the method for multiple target assays in accordance with the present invention.
Figure 2:
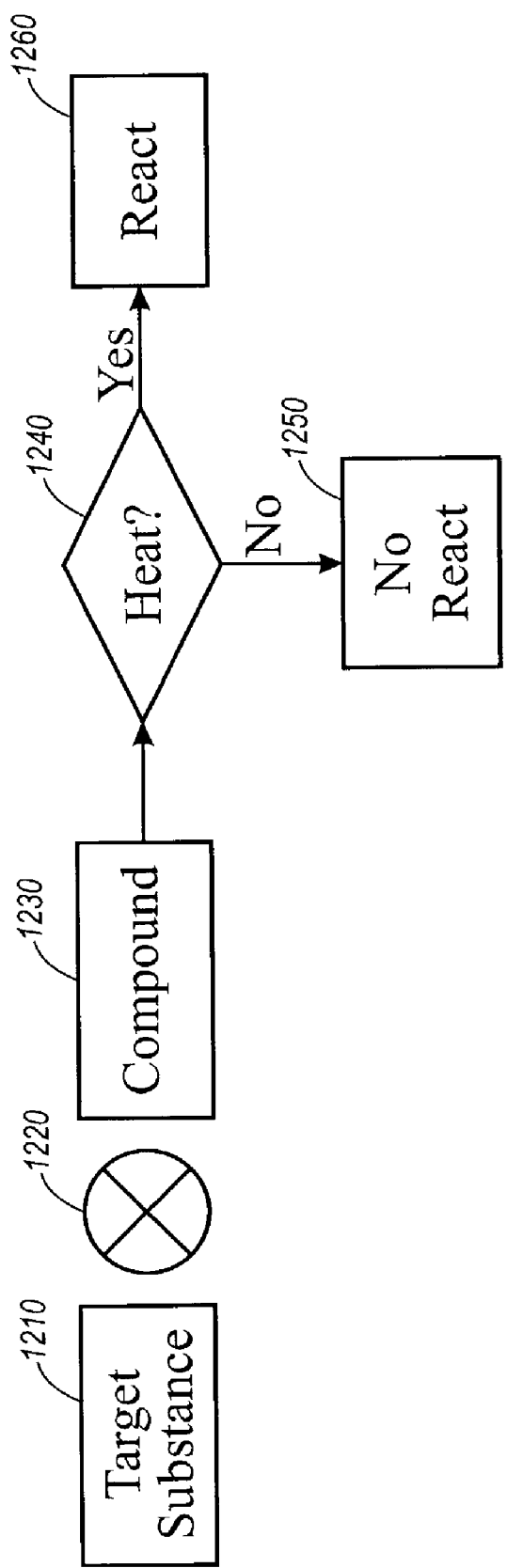
FIG. 2 shows steps in a lead profiling assay.

As used herein, the term "ligand" refers to an agent that binds a target molecule. According to the present invention, a ligand is not limited to an agent that binds a recognized functional region of the target protein e.g. the active site of an enzyme, the antigen-combining site of an antibody, the hormone-binding site of a receptor, a cofactor-binding site, and the like. In practicing the present invention, a ligand can also be an agent that binds any surface or conformational domains of the target protein. Therefore, the ligands of the present invention encompass agents that in and of themselves may have no apparent or known biological function, beyond their ability to bind to the target protein in the manner described above.

As used herein, the term "test ligand" refers to an agent, comprising a compound, molecule or complex, which is being tested for its ability to bind to a target molecule. Test ligands can be virtually any agent, including without limitation metals, peptides, proteins, lipids, polysaccharides, nucleic acids, small organic molecules, and combinations thereof. Complex mixtures of substances such as natural product extracts, which may include more than one test ligand, can also be tested, and the component that binds the target molecule can be purified from the mixture in a subsequent step.

As used herein, the term "target protein" refers to a peptide, protein or protein complex for which identification of a ligand or binding partner is desired. Target proteins include without limitation peptides or proteins known or believed to be involved in the etiology of a given disease, condition or pathophysiological state, or in the regulation of physiological function. Target proteins may be derived from any living organism, such as a vertebrate, particularly a mammal and even more particularly a human. For use in the present invention, it is not necessary that the protein's biochemical function be specifically identified. Target proteins include without limitation receptors, enzymes, oncogene products, tumor suppressor gene products, vital proteins, and transcription factors, either in purified form or as part of a complex mixture of proteins and other compounds. Furthermore, target proteins may comprise wild type proteins, or, alternatively, mutant or variant proteins, including those with altered stability, activity, or other variant properties, or hybrid proteins to which foreign amino acid sequences, e.g. sequences that facilitate purification, have been added.

As used herein, "test combination" refers to the combination of a test ligand and a target protein. "Control combination" refers to the target protein in the absence of a test ligand.

As used herein, "screening" refers to the testing of a multiplicity of molecules or compounds for their ability to bind to a target molecule.

As used herein, the term "lead molecule" refers to a molecule or compound, from a combinatorial library or other collection, which displays relatively high affinity for a target molecule. High affinity is detected by this invention through the heat released in a chemical reaction. The terms "lead compound" and "lead molecule" are synonymous.

As used herein, the term "target molecule" encompasses peptides, proteins, nucleic-acids, protein-nucleic acid complexes, and other receptors. The term encompasses both enzymes and proteins, which are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded, or triple-stranded. The term encompasses a nucleic acid which is a synthetic oligonucleotide, a portion of a recombinant DNA molecule, or a portion of chromosomal DNA. The term target molecule also encompasses portions of peptides, secondary, tertiary, or quaternary structure through folding, with substituents including, but not limited to, cofactors, coenzymes, prosthetic groups, lipids, oligosaccharides, or phosphate groups.

As used herein, the term "molecule" refers to the compound, which is tested for binding affinity for the target molecule. This term encompasses chemical compounds of any structure, including, but not limited to nucleic acids and peptides. More specifically, the term "molecule" encompasses compounds in a compound or a combinatorial library. The terms "molecule" and "ligand" are synonymous.

As used herein, the term "thermal change" encompasses the release of energy in the form of heat or the absorption of energy in the form of heat.

As used herein, the term "contacting a target molecule" refers broadly to placing the target molecule in solution with the molecule to be screened for binding. Less broadly, contacting refers to the turning, swirling, shaking or vibrating of a solution of the target molecule and the molecule to be screened for binding. More specifically, contacting refers to the mixing of the target molecule with the molecule to be tested for binding. Mixing can be accomplished, for example, by repeated uptake and discharge through a pipette tip or by deposition by robotic means. Preferably, contacting refers to the equilibration of binding between the target molecule and the molecule to be tested for binding.

As used herein, the term "biochemical conditions" encompasses any component, thermodynamic property, or kinetic property of a physical, chemical, or biochemical reaction. Specifically, the term refers to conditions of temperature, pressure, protein concentration, pH, ionic strength, salt concentration, time, electric current, potential difference, and concentrations of cofactor, coenzyme, oxidizing agents, reducing agents, detergents, metal ion, ligands, buffer components, co-solvents including DMSO (dimethyl sulfoxide), glycerol, and related compounds, enhancers, and inhibitors.

The present invention encompasses nanocalorimeters and nanocalorimeter arrays that enable measurement of enthalpic changes, such as enthalpic changes arising from reactions, phase changes, changes in molecular conformation, and the like. Furthermore, the present invention encompasses combinatorial methods and high-throughput screening methods that use nanocalorimeters in the study, discovery, and development of new compounds, materials, chemistries, and chemical processes, as well as high-throughput monitoring of compounds or materials, or high-throughput monitoring of the processes used to synthesize or modify compounds or materials. The present invention also relates to compounds or materials identified by the above methods and their therapeutic uses (for diagnostic, preventive or treatment purposes), uses in purification and separation methods, and uses related to their novel physical or chemical properties. For the purposes herein, a nanocalorimeter refers to a device capable of measuring heats of reaction in the range of nanocalories.

As an example, the present invention encompasses high-throughput screening methods for identifying a ligand that binds a target protein. If the target protein to which the test ligand binds is associated with or causative of a disease or condition, the ligand may be useful for diagnosing, preventing or treating the disease or condition. A ligand identified by the present method can also be one that is used in a purification or separation method, such as a method that results in purification or separation of the target protein from a mixture. The present invention also relates to ligands identified by the present method and their therapeutic uses (for diagnostic, preventive or treatment purposes) and uses in purification and separation methods.

In practicing the present invention, the test ligand is combined with a target molecule, and the mixture is maintained under appropriate conditions and for a sufficient time to allow binding of the test ligand to the target molecule. Experimental conditions are determined empirically for each target molecule. When testing multiple test ligands, incubation conditions are usually chosen so that most ligand:target molecule interactions would be expected to proceed to completion. In high-throughput screening applications, the test ligand is usually present in molar excess relative to the target molecule. The target molecule can be in a soluble form, or, alternatively, can be bound to a solid phase matrix. The matrix may comprise without limitation beads, membrane filters, plastic surfaces, or other suitable solid supports.

Binding to a given target is a prerequisite for pharmaceuticals intended to modify directly the action of that target. Thus, if a test ligand is shown, through use of the present method, to bind a target that reflects or affects the etiology of a condition, it may indicate the potential ability of the test ligand to alter target function and to be an effective pharmaceutical or lead compound for the development of such a pharmaceutical. Alternatively, the ligand may serve as the basis for the construction of hybrid compounds containing an additional component that has the potential to alter the target's function. For example, a known compound that inhibits the activity of a family of related enzymes may be rendered specific to one member of the family by conjugation of the known compound to a ligand, identified by the methods of the present invention, that binds specifically to that member at a different site than that recognized by the known compound.

The fact that the present method is based on physicochemical properties common to most targets gives it widespread application. The present invention can be applied to large-scale systematic high-throughput procedures that allow a cost-effective screening of many thousands of test ligands. Once a ligand has been identified by the methods of the present invention, it can be further analyzed in more detail using known methods specific to the particular target used. Also, the ligand can be tested for its ability to influence, either positively or negatively, a known biological activity of the target.

In the drug discovery process, a drug target is screened to determine if it will interact to a specified level with a large number, perhaps 500,000, of compounds from a drug library of compounds. Often it is desirable to screen several different drug targets against the same library of compounds if the targets are thought to have a similar function. In a competitive screen, the reaction of the drug library compound with the target prevents the reaction of a second known active compound that contains a detectable label such as, in the case of a fluorescent assay, a fluorescent label. This second reactive compound is often referred to as a labeled ligand. The level of reactivity of the drug library compound is inferred by detecting the fluorescence coming from the labeled ligand that binds to the target. Several types of fluorescent assays are currently utilized in the art, but the two most practiced are fluorescence intensity and fluorescence polarization.

In a fluorescence intensity assay, a labeled ligand at a low concentration and one or more drug library compounds at a higher concentration (5 µM) are mixed with a target. The labeled ligand is known to interact strongly with the target and is often the natural ligand. The label on the ligand in this example is a molecule that fluoresces in a particular way when stimulated by light such as a laser or an ultraviolet light source. Radioactive or chemiluminescent compounds can also be used as labels. The target is immobilized to the container and incubated with the mixture of labeled ligand and one or more drug library compounds to form the test compound. Following incubation, the free test compound is removed by washing, and the amount of labeled ligand is measured by detecting the amount and nature of the light emitted from the fluorescent label attached to the ligand. If the fluorescence is reduced, then a reaction with a drug library compound has occurred. The reaction will reduce the amount of labeled ligand that reacts by a predicted amount ranging from at least 20% to 50% or more. If the fluorescence is not reduced, then a reaction has not occurred, since the labeled ligand reaction is not inhibited. The variation in the amount of fluorescent light for uninhibited binding is approximately 10%, resulting in an acceptable signal to noise ratio.

For the fluorescence polarization approach, the labeled ligand is incubated with the receptor and the drug library compounds, but the receptor does not need to be immobilized. Here the assay relies on the observation that fluorescence from the labeled ligand bound to the receptor is substantially more polarized than the fluorescence from an unbound labeled ligand. Again in this approach as in general for competitive assays, the signal produced is maximum when no drug library compounds bind to the target receptor.

Since several targets can be screened against the same libraries, it is desirable to do this screening simultaneously. This is especially true since the probability of a reaction is low, typically less than 0.1%, so with a small number of targets (5) tested together, having several targets react with a small number of drug library compounds in a given test is statistically unlikely. With competitive assays, however, since the measured signal is maximum in the case where there is no reaction, and decreases partially with a reaction, screening with multiple targets leads to a large signal for each of the non reacting targets that is reduced only by an amount due to inhibition by one reacting target. This reduction is now a much smaller percentage of the total signal than it was in the case of a single target and results in a substantially degraded signal to noise level. For example, a 50% signal reduction in signal for reaction to a single target becomes only a 10% reduction in total signal for five targets, which is an unacceptable level. Although alternative methods such as using different fluorophores on each labeled ligand with non-overlapping emission spectra could be employed, these would increase the amount of time and effort required for assay development.

However, with the device taught herein, there is no need to develop a specific assay, since a direct measurement of the heat of interaction is made utilizing calorimetry. Calorimetric measurements produce no signal unless there is a reaction. Hence, the amount of signal produced for a single reaction with multiple targets is identical to the amount for just one target. Consequently, multiple targets do not degrade the signal to noise. Turning now to FIG. 1, there is shown an embodiment of the nanocalorimeter as used for a multiple target assay for drug discovery. In FIG. 1, a sample containing a plurality of targets Ti is merged with a sample containing one or more drug candidates Lj at step 1110. A measurement is made at step 1120 to determine if a reaction has occurred. If no reaction has occurred, the test results are recorded at step 1130. If a reaction is detected through heat released, the candidates and targets are then screened separately, as shown at step 1140. If a reaction is not detected at step 1150, then the test result is recorded at step 1170. If a reaction is detected for an individual test, the result is recorded at step 1160. Because the probability of a reaction at step 1120 is typically less than 0.1%, very few additional experiments are required, enabling a large reduction in the total number of screening reactions. For example, if five targets are screened by 500,000 candidate compounds individually, then 2,500,000 separate screening experiments need to be performed while only 500,000 screens are performed if 5 targets are tested simultaneously. At a 0.1% hit rate for each target, this results in the need to reexamine 2500 experiments by expanding each of them into a matrix of 5 unique combinations which translates into 12,500 individual screening experiments for a total of 512,500 screens. This represents a savings of nearly two million screening tests.

Using several candidate compounds in each screening experiment can further reduce the number of screen reactions. For example, with 5 candidate compounds in each screen experiment, then 500,000 screens are needed to screen 500,000 drug compounds against 5 targets without target multiplexing and 100,000 screen experiments with target multiplexing. In both cases about 2500 reactions will be measured and need to be reexamined with only one target and drug compound. For the case with no multiplexing this results in an additional 12,500 screen experiments or a total of 512,500 experiments. In the case of multiplexed targets, this results in an additional 62,500 screen experiments resulting in a total of 162,500 screen experiments.

While the present invention has been illustrated and described with reference to specific embodiments, further modification and improvements will occur to those skilled in the art. It is to be understood, therefore, that this invention is not limited to the particular forms illustrated and that it is intended in the appended claims to embrace all alternatives, modifications, and variations which do not depart from the spirit and scope of this invention.

What is claimed is:

1. A method of drug discovery utilizing a nanocalorimeter, the method comprising:

depositing at least one drop containing a plurality of drug targets and at least one drop containing a plurality of drug candidates upon a nanocalorimeter test substrate, each drop having a volume in a range between approximately 20 nL and approximately 250 µL;

merging said at least one drop containing a plurality of drug targets and said at least one drop containing a plurality of drug candidates by applying a voltage to drop merging electrodes and producing a mixture containing the plurality of drug targets and the plurality of drug candidates;

calorimetrically measuring heat from the mixture while maintaining the mixture under appropriate conditions for a sufficient time to allow binding;

from the calorimetrically measured heat, detecting whether a reaction has occurred in the mixture resulting in thermal change; and if a reaction has occurred, performing additional screening to identify at least one of the drug candidates in the mixture that reacted with one of the drug targets; the additional screening including:
individually testing with each other a single one of the drug targets that was present in the mixture that reacted and a single one of the drug candidates that was present in the mixture that reacted; and
detecting whether a reaction occurs between the single one of the drug targets and the single one of the drug candidates.

2. The method according to claim 1, wherein the drops contain low concentrations of said drug targets and said drug candidates.

3. The method according to claim 1, wherein the nanocalorimeter utilizes a single test chamber to perform the acts of depositing, merging, and calorimetrically measuring.

4. The method according to claim 1, wherein the nanocalorimeter utilizes a loading chamber and a separate test chamber to perform the acts of depositing, merging, and calorimetrically measuring.

5. A method of drug discovery utilizing a nanocalorimeter, the method comprising:
depositing at least one drop containing a plurality of drug targets and at least one drop containing a plurality of drug candidates upon a nanocalorimeter test substrate, each drop having a volume of approximately 20 nL or more;
merging said at least one drop containing a plurality of drug targets and said at least one drop containing a plurality of drug candidates on the test substrate to produce a mixture containing the plurality of drug targets and the plurality of drug candidates, the mixture including less than 500 μL of volume;
producing a heat signal by calorimetrically measuring temperature from the test substrate, the heat signal indicating thermal change in the mixture, the heat signal not being degraded due to said plurality of drug targets in the mixture;
from the heat signal, detecting whether a reaction has occurred in the mixture; and
if a reaction has occurred, performing additional screening to identify at least one of the drug candidates in the mixture that reacted with one of the drug targets; the additional screening including:
individually testing with each other a single one of the drug targets that was present in the mixture that reacted and a single one of the drug candidates that was present in the mixture that reacted; and
detecting whether a reaction occurs between the single one of the drug targets and the single one of the drug candidates.

6. The method according to claim 5, wherein performing additional screening comprises:
depositing a drop containing at least one drug target upon a test substrate;
depositing a drop containing at least one drug candidate upon said test substrate;
merging said drop containing at least one drug target and said drop containing at least one drug candidate by applying a voltage to drop merging electrodes; and
detecting whether a reaction has occurred between said drop containing at least one drug target and said drop containing at least one drug candidate by measuring the temperature difference from before said reaction to after said reaction.

7. The method according to claim 6, wherein said drop containing at least one drug target contains a single drug target.

8. The method according to claim 6, wherein said drop containing at least one drug candidate contains a single drug candidate.

9. The method according to claim 6, further comprising identifying those drug candidates that cause a reaction.

10. The method according to claim 6, wherein merging said drop containing a plurality of drug targets and said drop containing a plurality of drug candidates comprises utilizing electrostatic force.

11. The method according to claim 5, wherein detecting whether a reaction has occurred comprises detecting an increase in signal proportional to the reaction.

12. The method according to claim 5, wherein detecting whether a reaction has occurred comprises detecting a thermal change.

13. The method according to claim 5, further comprising providing a controlled environment.

14. The method according to claim 13, wherein said controlled environment comprises a thermally controlled environment.

15. The method according to claim 5, wherein merging said at least one drop containing a plurality of drug targets and said at least one drop containing a plurality of drug candidates comprises utilizing electrostatic force.

16. The method according to claim 5, wherein the nanocalorimeter test substrate has at least one reference region and at least one measurement region.

17. The method according to claim 16, wherein depositing said at least one drop containing a plurality of drug targets comprises depositing at least one drop containing a plurality of drug targets within each of said measurement region and said reference region.

18. The method according to claim 16, wherein depositing said at least one drop containing a plurality of drug candidates comprises depositing at least one drop containing a plurality of drug candidates within said measurement region.

19. The method according to claim 16, further comprising depositing at least one drop of a non-reactive chemical material within said reference region.

20. A method of drug discovery utilizing a nanocalorimeter, the method comprising:
depositing a respective drop containing a plurality of drug targets and a respective drop containing a plurality of drug candidates upon a measurement region of a nanocalorimeter test substrate and depositing a respective drop containing a plurality of drug targets and a respective drop of non-reactive chemical material upon a reference region of the test substrate, the measurement region and the reference region being thermally isolated, each drop having a volume of approximately 20 nL or more;
merging the measurement region's respective drops in the measurement region and the reference region's respective drops in the reference region to produce a respective mixture in each of the measurement region and the reference region, each respective mixture including less than 500 μL of volume; the measurement region's respective mixture containing the plurality of drug targets and the plurality of drug candidates;
maintaining the measurement region's respective mixture under appropriate conditions and for a sufficient time to allow binding of each candidate in the plurality of drug candidates to each target in the plurality of drug targets, binding of any of the candidates to any of the targets resulting in a temperature difference;
producing a heat signal indicating thermal change due to binding in the measurement region, the heat signal not being degraded due to said plurality of drug targets in the mixture; the act of producing the heat signal comprising:

calorimetrically measuring temperature both from the measurement region and from the reference region; and obtaining a difference signal indicating difference between measured temperatures of the measurement and reference regions;

from the heat signal, detecting whether a reaction has occurred between said plurality of drug candidates and said plurality of drug targets in the measurement region's mixture; and if a reaction has occurred, performing additional screening to identify at least one of the drug candidates in the measurement region's mixture that reacted with one of the drug targets; the additional screening including:

individually testing with each other a single one of the drug targets that was present in the mixture that reacted and a single one of the drug candidates that was present in the mixture that reacted; and detecting whether a reaction occurs between the single one of the drug targets and the single one of the drug candidates.

* * * * *